(12) United States Patent
Domanski et al.

(10) Patent No.: US 6,582,382 B2
(45) Date of Patent: Jun. 24, 2003

(54) ORTHOPEDIC SUPPORTS

(75) Inventors: Edward M. Domanski, Batavia, OH (US); Cindy Lamping, Cincinnati, OH (US); Lloyd Bruce, Cincinnati, OH (US); Sherry Ann Hinds, Goshen, OH (US); Stefan Bodenschatz, Buxtehude (DE)

(73) Assignee: Beiersdorf, Inc., Mariemont, OH (US)

( * ) Notice: Subject to any disclaimer, the term of this patent is extended or adjusted under 35 U.S.C. 154(b) by 158 days.

(21) Appl. No.: 09/783,840

(22) Filed: Feb. 16, 2001

(65) Prior Publication Data
US 2002/0115950 A1 Aug. 22, 2002

(51) Int. Cl.[7] .................................................. A61F 5/00
(52) U.S. Cl. .................. 602/1; 602/5; 602/20; 602/23
(58) Field of Search ............. 602/22–23, 20–24, 602/26–29, 60–62, 65, 1, 5; 128/881–882

(56) References Cited

U.S. PATENT DOCUMENTS

| | | |
|---|---|---|
| 2,287,821 A | 6/1942 | O'Donovan |
| 2,641,761 A | 6/1953 | Schultz |
| 3,084,685 A | 4/1963 | Lewis |
| 3,318,305 A | 5/1967 | Schultz |
| 3,327,703 A | 6/1967 | Gamm |
| 4,013,070 A * | 3/1977 | Harroff .................. 602/21 |
| 4,048,991 A | 9/1977 | Marx |
| 4,084,584 A | 4/1978 | Detty |
| D259,955 S | 7/1981 | Helferich |
| 4,287,885 A | 9/1981 | Applegate |
| 4,294,240 A | 10/1981 | Thill |
| 4,474,573 A | 10/1984 | Detty |
| 4,494,247 A | 1/1985 | Kelly |
| 4,532,921 A | 8/1985 | von Torklus et al. |
| 4,762,123 A | 8/1988 | Dedo |
| 4,832,010 A | 5/1989 | Lerman |
| 4,844,058 A | 7/1989 | Vogelbach |
| 4,961,418 A | 10/1990 | McLaurin-Smith |
| 4,966,137 A | 10/1990 | Davini |

(List continued on next page.)

*Primary Examiner*—Michael A. Brown
*Assistant Examiner*—Lalita M Hamilton
(74) *Attorney, Agent, or Firm*—Norris, McLaughlin & Marcus

(57) ABSTRACT

Orthopedic supports comprising foam material, such as neoprene, and textile spacers wherein the textile spacer is interspaced between pieces of foam material, and the textile spacer and foam material are secured together. The orthopedic supports can be configured to conform to any of body part such as knee, wrist or ankle supports. The orthopedic supports can be used to provide therapeutic support and compression to the joint of a user.

20 Claims, 13 Drawing Sheets

U.S. PATENT DOCUMENTS

| | | |
|---|---|---|
| 4,986,263 A | 1/1991 | Dickerson et al. |
| 4,991,234 A | 2/1991 | Greenberg |
| 5,036,838 A | 8/1991 | Sherman |
| 5,058,573 A | 10/1991 | Hess et al. |
| 5,092,318 A | 3/1992 | More et al. |
| 5,154,690 A | 10/1992 | Shiono |
| 5,168,577 A * | 12/1992 | Detty ............................. 2/16 |
| 5,306,229 A | 4/1994 | Brandt et al. |
| 5,334,135 A | 8/1994 | Grim et al. |
| 5,372,575 A | 12/1994 | Sebastian |
| 5,413,553 A | 5/1995 | Downes |
| 5,472,414 A | 12/1995 | Detty |
| 5,474,524 A | 12/1995 | Carey |
| 5,478,306 A | 12/1995 | Stoner |
| 5,620,413 A | 4/1997 | Olson |
| 5,667,484 A | 9/1997 | Brossard |
| 5,695,452 A | 12/1997 | Grim et al. |
| 5,728,057 A | 3/1998 | Ouellette et al. |
| 5,735,807 A | 4/1998 | Cropper |
| 5,769,803 A | 6/1998 | Brossard |
| 5,843,010 A | 12/1998 | Bodmer |
| 5,853,380 A | 12/1998 | Miller |
| 5,891,079 A | 4/1999 | Barnes |
| 5,897,518 A | 4/1999 | Shaw |
| 5,897,520 A | 4/1999 | Gerig |
| 5,899,872 A | 5/1999 | Gilmour |
| 5,921,949 A | 7/1999 | Dray |
| 5,944,678 A | 8/1999 | Hubbard |
| 6,059,744 A | 5/2000 | Hardt |
| 2001/0007929 A1 | 7/2001 | Schlomski |

\* cited by examiner

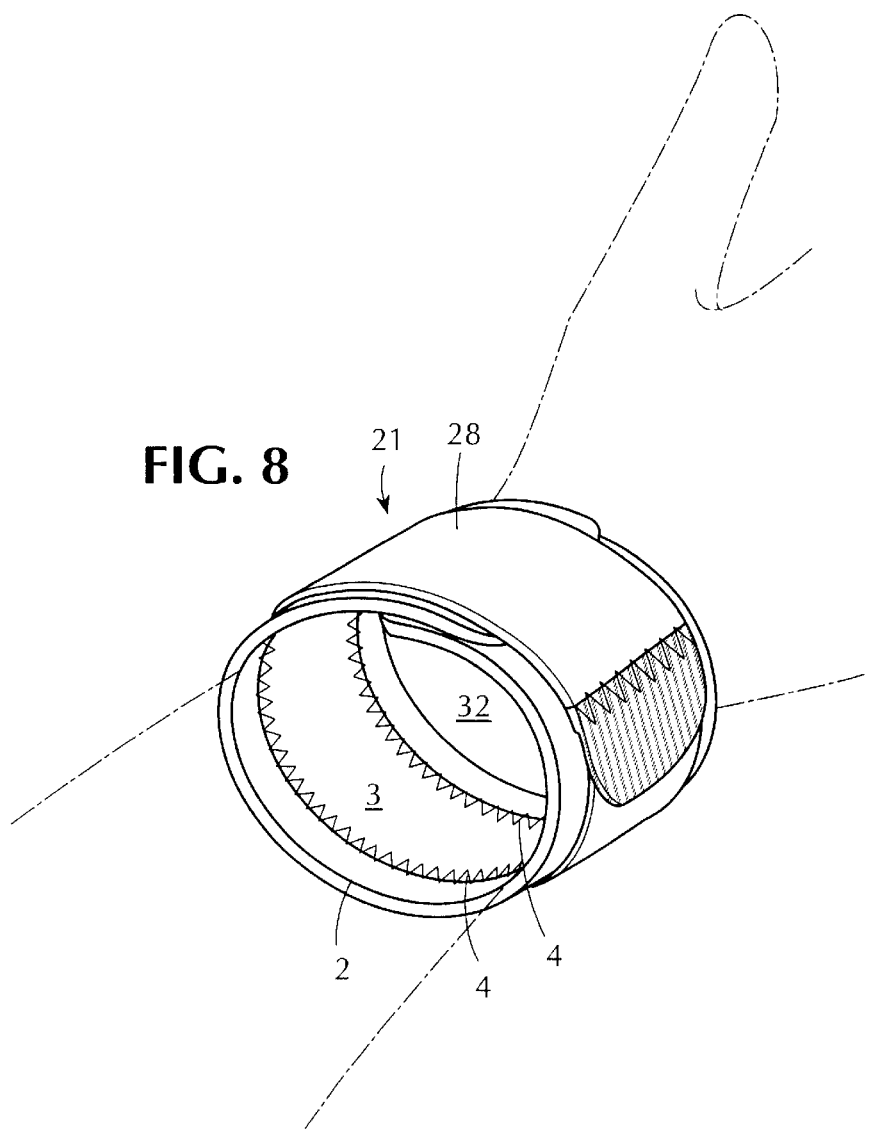
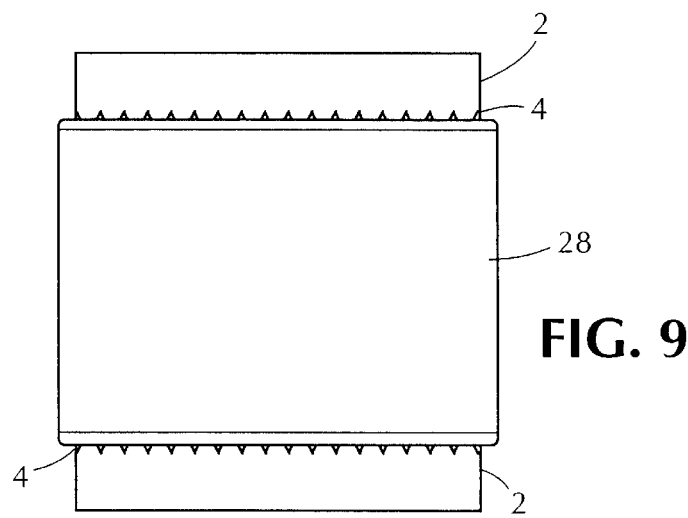

ORTHOPEDIC SUPPORTS

BACKGROUND OF THE INVENTION

The invention concerns orthopedic supports that are made from foam material with air permeable textile spacers, and the use thereof. The devices can be configured or adapted to provide orthopedic support to any part of the body requiring therapy.

SUMMARY OF THE INVENTION

The orthopedic supports comprise foam material, such as neoprene, and textile spacers made from textile material or fabric. Generally, the textile spacer is interspaced between pieces of foam spacer, and the textile spacer and foam material are secured together. The orthopedic supports can be configured to conform to any number of body parts, and in the preferred embodiments, the orthopedic supports are configured as knee, wrist or ankle supports.

DETAILED DESCRIPTION OF THE DRAWINGS

FIG. 8 is a perspective view of an example of a wrist support according to the invention depicting the wrist of a user.

FIG. 9 is a bottom view of an example of a wrist support according to the invention.

DETAILED DESCRIPTION OF THE INVENTION

The orthopedic supports comprise foam material, such as neoprene, laminated neoprene and like foamed cell polymers or rubber materials in combination with textile spacers made from textile material or fabric. Generally, the supports have strips or pieces of neoprene material with textile spacers interspaced between the neoprene strips or pieces such that the textile spacers and neoprene strips form a generally square or rectangular shape having an upper lateral side and a lower lateral side of foam material and first and second ends of foam material and textile spacer. The first end and/or second end can be secured to each other, other components and/or the upper lateral side and/or lower lateral side to configure the orthopedic supports. The components of the supports are secured together by attaching means, such as stitching, adhesive materials, binders, welding and the like and can be configured to accommodate various parts of the body, such as the ankle, knee or wrist.

Figure 1:
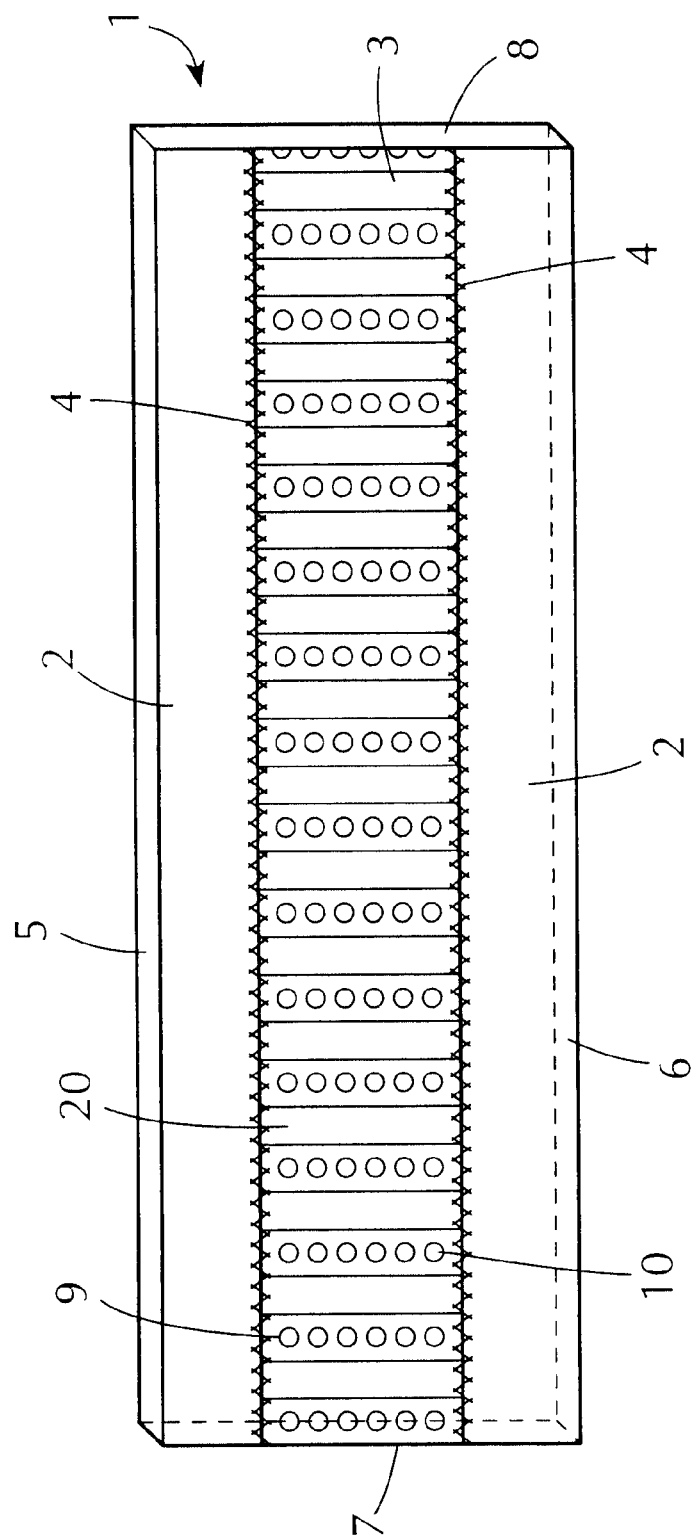
FIG. 1 is a perspective view of an embodiment wherein the orthopedic support comprises two pieces of foam material and a textile spacer.

The orthopedic supports are made from a combination of materials comprising at least one textile spacer and at least one, preferably more than one, piece of foam material. An example of the combination of materials is shown in FIG. 1 as 1 comprising two pieces of foam material 2 and one textile spacer 3 which are secured together by attaching means 4 to form a rectangular shaped combination of materials having an upper lateral side 5, lower lateral side 6, a first end 7 and a second end 8.

The foam material is selected to have support and compression characteristics to the joint or other location of the user's body where the support is applied. Any open or closed cell foam having stretch and recovery properties can be used. Neoprene is preferably used in the orthopedic support to provide support and compression. Other preferred foam materials are material having similar stretch and recovery properties as neoprene. The textile spacer and foam material are generally the same thickness, however the components may have a difference in thickness of up to about 4 millimeters.

The foam material, such as neoprene material, may be laminated to provide a moisture barrier for the orthopedic support and to provide a soft lining for comfort. The laminate is generally light weight circular knit nylon or other textile material having acceptable elongation and comfort. The laminate is selected such that it will not significantly impede the stretch and recovery properties of the foam material. The laminate material, or outer surface of the foam material, may also comprise all or components of a two part fastener system such as, on at least one side, hook engageable material, such as the loop portion of VELCRO® fastening material.

The material or fabric of the textile spacer is air permeable and moisture wicking, and allows for moisture transfer and/or moisture vapor transfer. This provides for an orthopedic support with comfort to the user and inhibits moisture from sweat at the support interface with the skin. Powerstretch Rx fabric available from Malden Mills Industries, Inc., Lawrence, Mass., USA. may be used for the textile spacer. In the preferred embodiments as shown in FIGS. 1–22, the outer surface of the textile spacer comprises one or more indented regions 9 and protrusions 20, such that the textile spacer has a ribbed appearance, with the indented regions optionally comprising a plurality of holes or openings 10 which aid to a degree in breathability. The outer surface of the textile spacer may also be engageable with fasteners, such as a two part hook and loop type fastener.

The combination of foam material and textile spacer provides a support that will have greater breathability compared to conventional supports and the combination of foam material and textile spacer will reduce or eliminate irritation or pressure sores that can be associated with other types of orthopedic supports. Also, interspacing textile spacer between foam material provides for an orthopedic support with a cleaner look that is more durable by eliminating fraying of the textile material at the ends and also can reduce irritation to the user that can result by use of conventional supports from frayed textile material or fabric. The combination of foam material and textile spacer provide an orthopedic support that has the support and compression characteristics that all foam or all textile material or fabric supports with numerous benefits over the art, such as those addressed above.

The orthopedic support is generally configured to conform to a body part or joint for support and compression purposes by attaching means, such as stitching, adhesive, binders, welding, and the like. The orthopedic supports may also comprise other components, such as at least one strap and, at least one fastener, including disengageable two part fastener systems such as VELCRO or similar hook and loop type fasteners for engaging the support with the body. Other types of disengageable fasteners that may be used are buckles, buttons, snaps and the like. In preferred embodiments the supports are configured as knee supports, wrist supports and ankle supports. As used in this Specification, the term "supports" is intended to have a broad application and includes any device for interacting with a joint, muscle or bone of the human body for therapeutic purposes, including supports, braces and bandages, as should be appreciated by one skilled in the art. Also, stitching is generally shown as the attaching means in the embodiments of the invention illustrated FIGS. 2–22, it being understood, however, that other types of attaching means, such as adhesive, bonding, welding and the like may also be used.

Referring now to FIGS. 2–7 there is shown an embodiment of the invention where the support is configured in the shape of a knee support 11. As shown in FIGS. 2–7, and particularly in FIGS. 2 and 4–6, the knee support comprises at least two pieces of foam material, preferably laminated neoprene, and at least one piece of textile spacer. The foam material and textile spacer are secured together by attaching means 4, which as shown in FIGS. 2 and 4–6 may be stitching, particularly stitching in a zig-zag type pattern. In addition to stitching, the attachment means 4 may be binders, welding or adhesive material. The knee support is formed in a generally cylindrical shape by securing together by vertical attaching means (not shown) the first end and the second end in a vertical direction at any point of the knee support. The vertical attaching means may be stitching, adhesive materials, binders, welding and the like.

The knee support is generally in the shape of a cylinder to interface with the corresponding knee of a user. As shown in FIGS. 2–7, the knee support comprises a front 12 and a back 13 with a top opening 14 and bottom opening 15. As shown in the figures, particularly FIG. 6, the knee support is generally in the shape of a hollow cylinder having a vertical dimension of the front 12 larger than that of the back 13 such that the top opening 14 and bottom opening 15 are angled towards each other from front 12 to back 13. This inhibits the knee support from bunching when the knee of the user is bent.

As shown in FIGS. 2–5 and 7, the knee support may have a patella opening 16 to accommodate the patella of a user. The shape of the opening will be generally round, but may be any shape which accommodates the patella of a user. Immediately adjacent to the opening is a patella pad 17 which is comprised of two pieces of textile material with foam material there between. The components of the patella pad 17 are held together by an opening stitch 18 which is circumferentially adjacent to the patella opening 16 and defines the patella opening 16 and a patella pad stitch 19 which is at the circumference of the end of the patella pad 17 circumferentially opposite the opening stitch 16. In the preferred embodiments of the invention, the opening stitch and patella pad stitch are in a zig-zag type pattern.

The textile spacer has one or more of indentations 9 and one or more protrusions 20. The indentations 9 have a plurality of holes 10. As shown in FIGS. 2 and 4–7, the indentations 9, protrusions 20 and holes 10 of the knee support exemplified in FIGS. 2–7 may be arranged in a vertical direction, that is being about perpendicular to the foam material 2. It is understood, however, that the indentations 9, protrusions 20 and holes 10 may be arranged in any direction.

Figure 2:
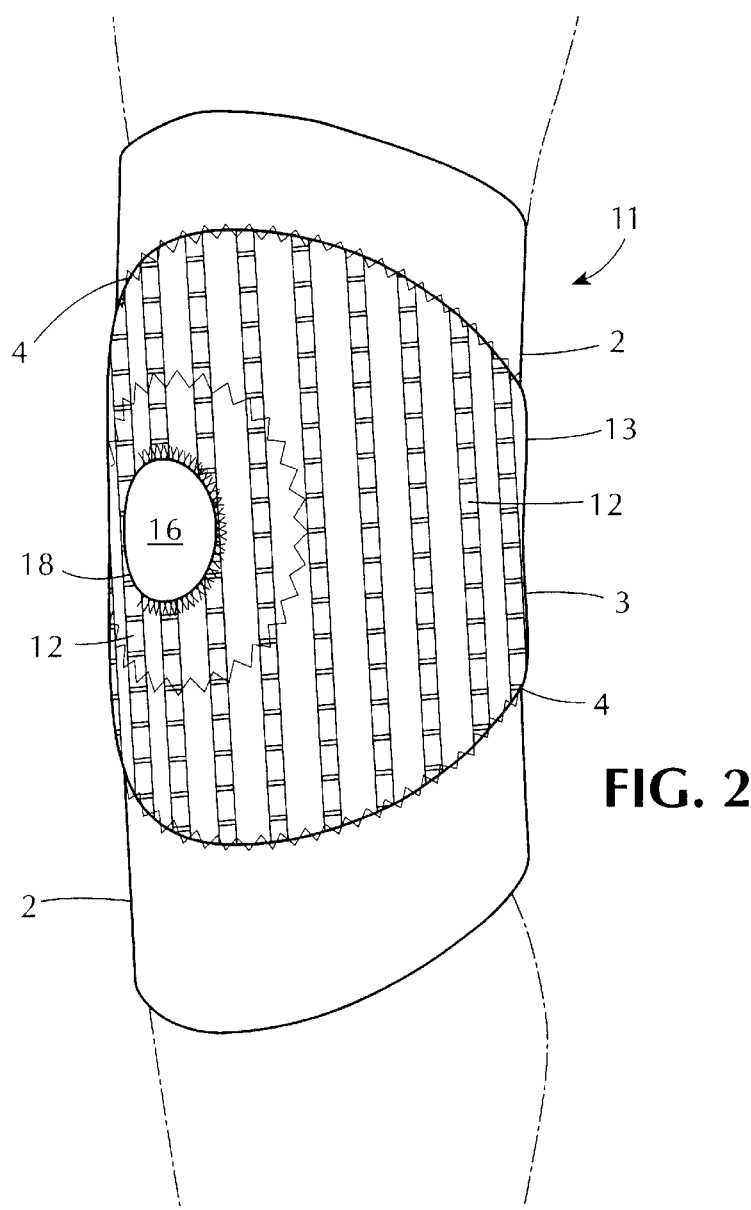
FIG. 2 is a perspective view of an example of a knee support according to the invention depicting the knee of a user.
Figure 3:
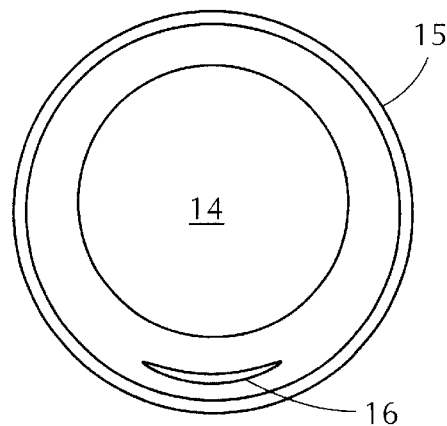
FIG. 3 is a bottom view of an example of a knee support according to the invention.
Figure 4:
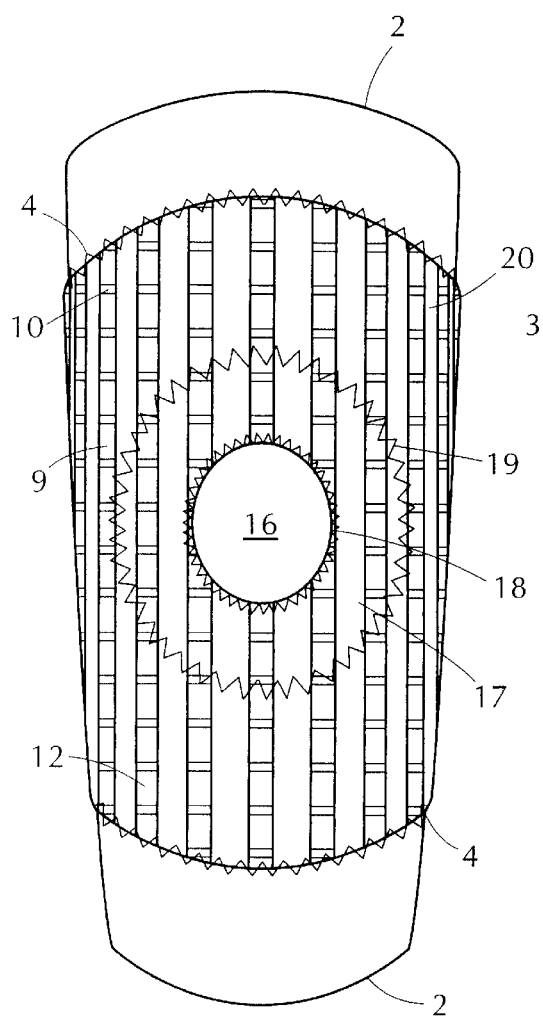
FIG. 4 is a front view of an example of a knee support according to the invention.
Figure 5:
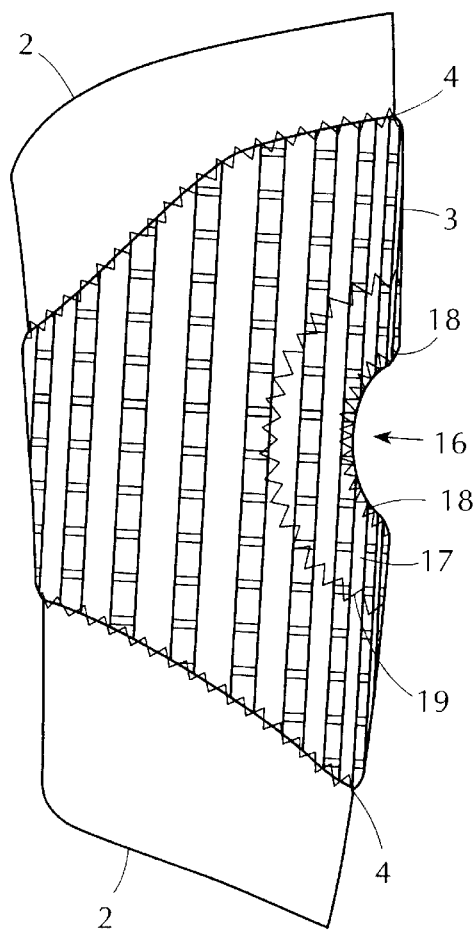
FIG. 5 is a side view of an example of a knee support according to the invention.
Figure 6:
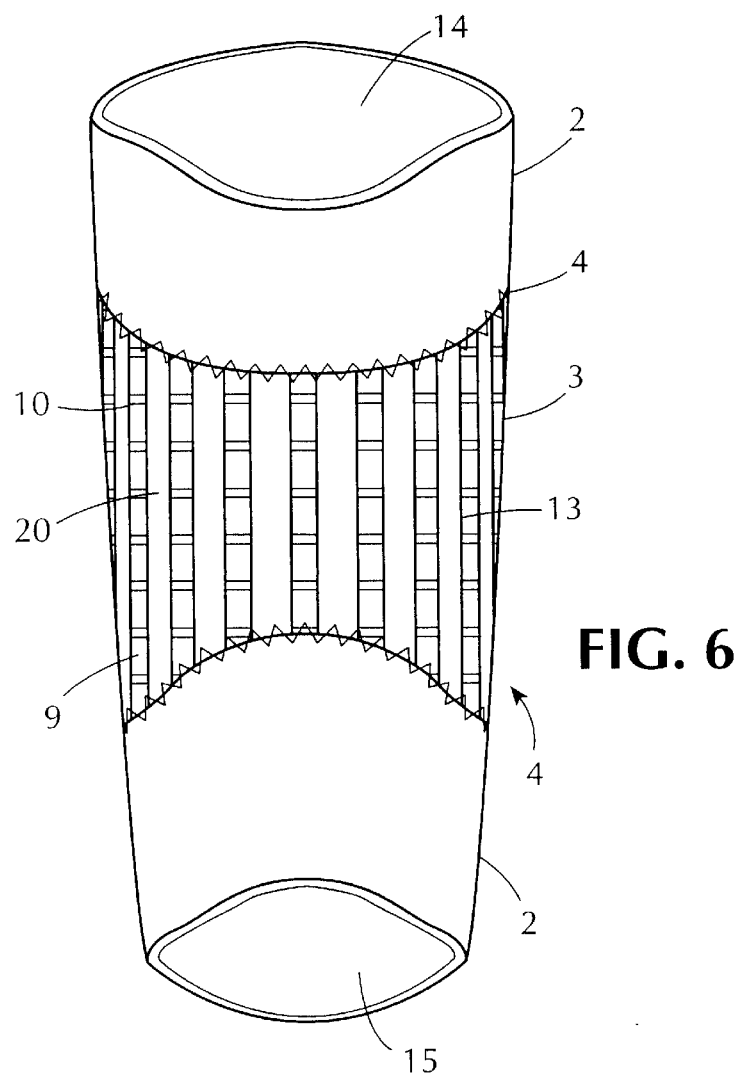
FIG. 6 is a back view of an example of a knee support according to the invention.
Figure 7:
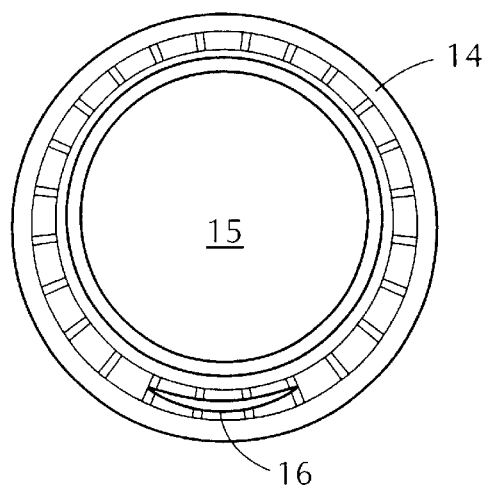
FIG. 7 is a top view of an example of a knee support according to the invention.
Figure 10:
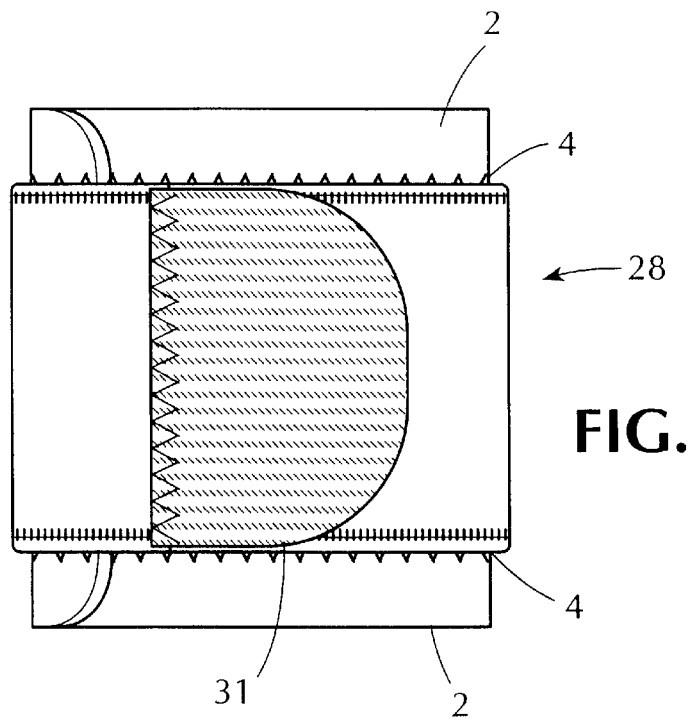
FIG. 10 is a top view of an example of a wrist support according to the invention.

As shown in FIG. 2, the user would slip the knee support 11 over the general region of the knee such that the front 12 is positioned at the front of the knee and the back 13 is positioned at the back of the knee. The user may apply the knee support such that all or part of the patella of the user is placed within the patella opening 16, with the center of the patella positioned at about the center of the patella opening 16.

An embodiment of the invention wherein the orthopedic support is configured in the form of a wrist support 21 is shown in FIGS. 8–13. As shown particularly in FIGS. 12 and 13, the exemplified wrist support comprises a body 22 having at least two pieces of foam material 2 and at least one piece of textile spacer 3. The textile spacer is the same as that described above with respect to the knee support, having one or more protrusions 20, one or more indentations 9 and a plurality of holes 10 and the other features and characteristics described above with respect to the knee support and otherwise. The foam materials and textile spacer are secured together by attaching means 4 and which as shown in FIGS. 8–10 and 12–13 may be stitching in a zig-zag type pattern. As would be understood by one skilled in the art, the wrist support can be formed into a generally cylindrical shape by securing the first end and second end of the combination of material by attaching means such as stitching, adhesive materials, binders, welding and the like (not shown). In an embodiment of the invention as illustrated in FIGS. 8–13, the first end and second end of the foam materials and textile spacer can be secured to a fastening mechanism 23 by second attaching means 27, which may be stitching, adhesive materials, binders, welding and the like, to form the generally cylindrically shaped wrist support. In the wrist support exemplified in FIGS. 8–13, the second attaching means may be stitching in a zig-zag type pattern.

As shown in FIGS. 8–13, the fastening mechanism 23 comprises a boxed portion 24 having at least two pieces of material and a stiffener (not shown). The material has a first boxed portion end 25a and second boxed portion end 25b and a first boxed portion side 26a and a second boxed portion side 26b. The first end 7 is secured to the first boxed portion end 25a and the second end 8 is secured to the second boxed portion end 25b, each generally by the second attaching means 27. The first boxed portion side 26a and second boxed portion side 26b are stitched together with the stiffener within the boxed portion 23. The stiffener could be of plastic, metal, paper or other suitable material.

The wrist support may also comprise a wrist support strap 28 which is shown in FIGS. 8–13. The wrist support strap comprises a flexible portion 29 having two ends 29a and 29b, which is generally made from knit or woven elastic textile material having an engageable fastening member 30, such as the loop portion of a two part hook and loop type fastener which may be laminated onto one or both sides of the material of the flexible portion 29 or may be part of one or both sides the material of the flexible portion 29 itself. Attached to the flexible portion 29 at one end 29b is securing portion 31 which may be part of a two part fastening system corresponding to the fastening member 30 of the flexible portion 29. The wrist support strap 28 is secured to the wrist support by having the end 29a of flexible portion 29 opposite to that of the securing portion 31 secured by the second attaching means 27. For example, as shown in FIGS. 8–13, the securing portion may be the loop portion of a two part fastener system, such as VELCRO and made from such material or laminates thereof. It being understood that the fastening member 30 could also be the loop portion of a two part fastener system with the securing portion 31 being the hook portion. Buckles, buttons, snaps or other types of disengageable materials may also be used.

Figure 11:
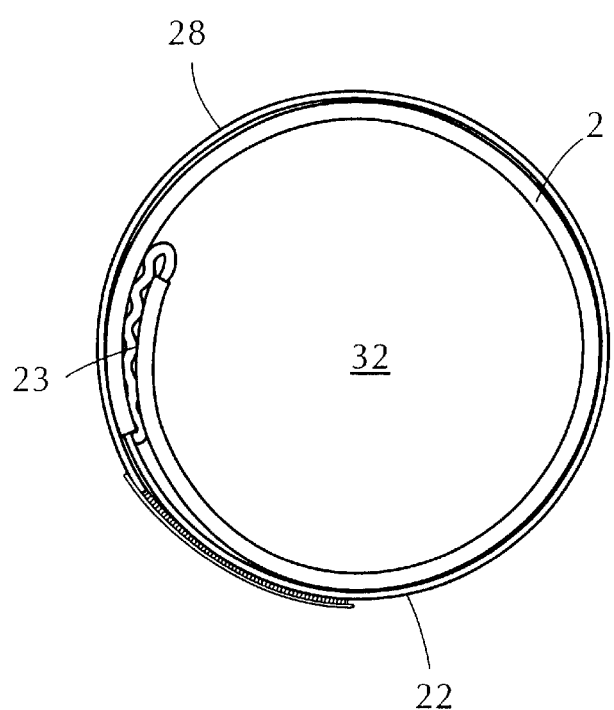
FIG. 11 is a side view of an example of a wrist support according to the invention.
Figure 12:
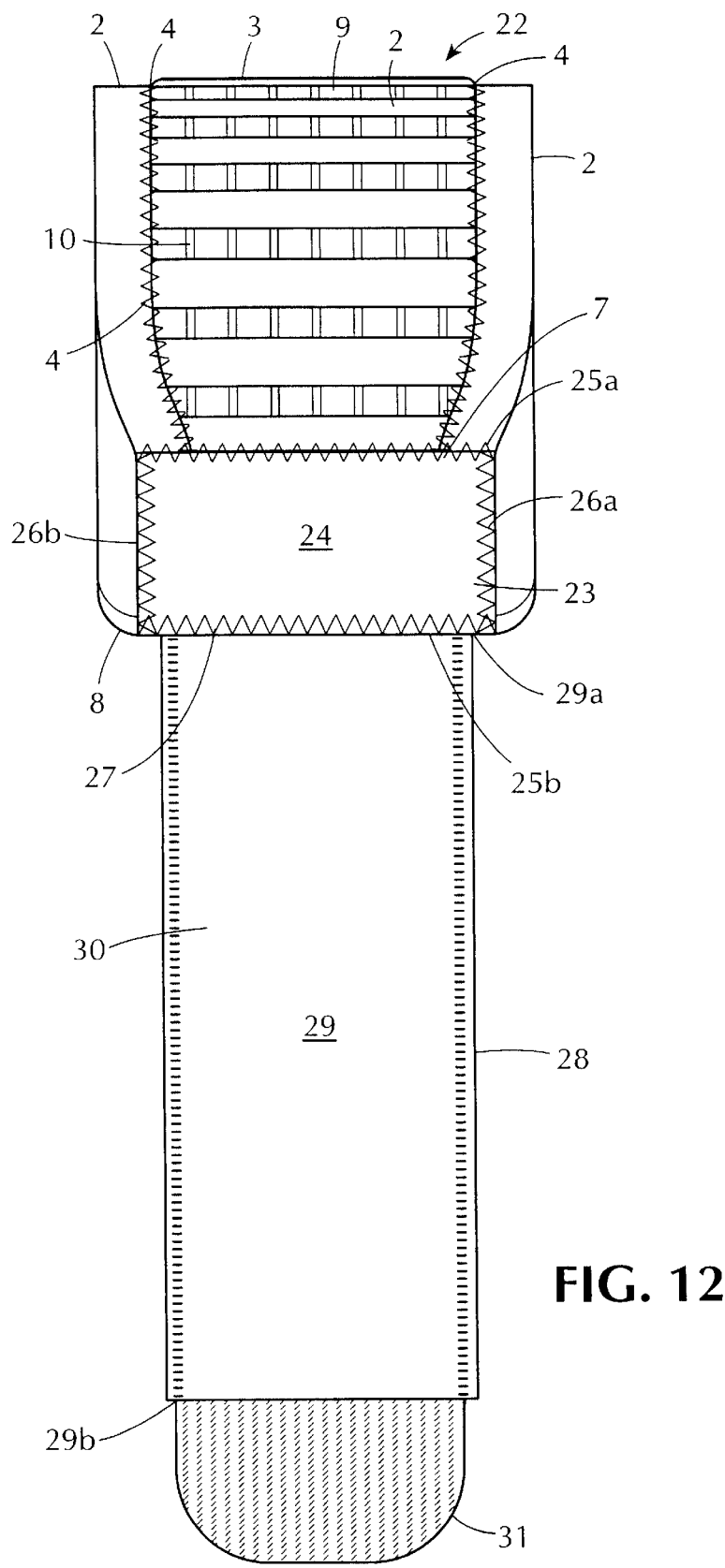
FIG. 12 is a top view of an example of a wrist support according to the invention with the wrist strap dis-engaged.
Figure 13:
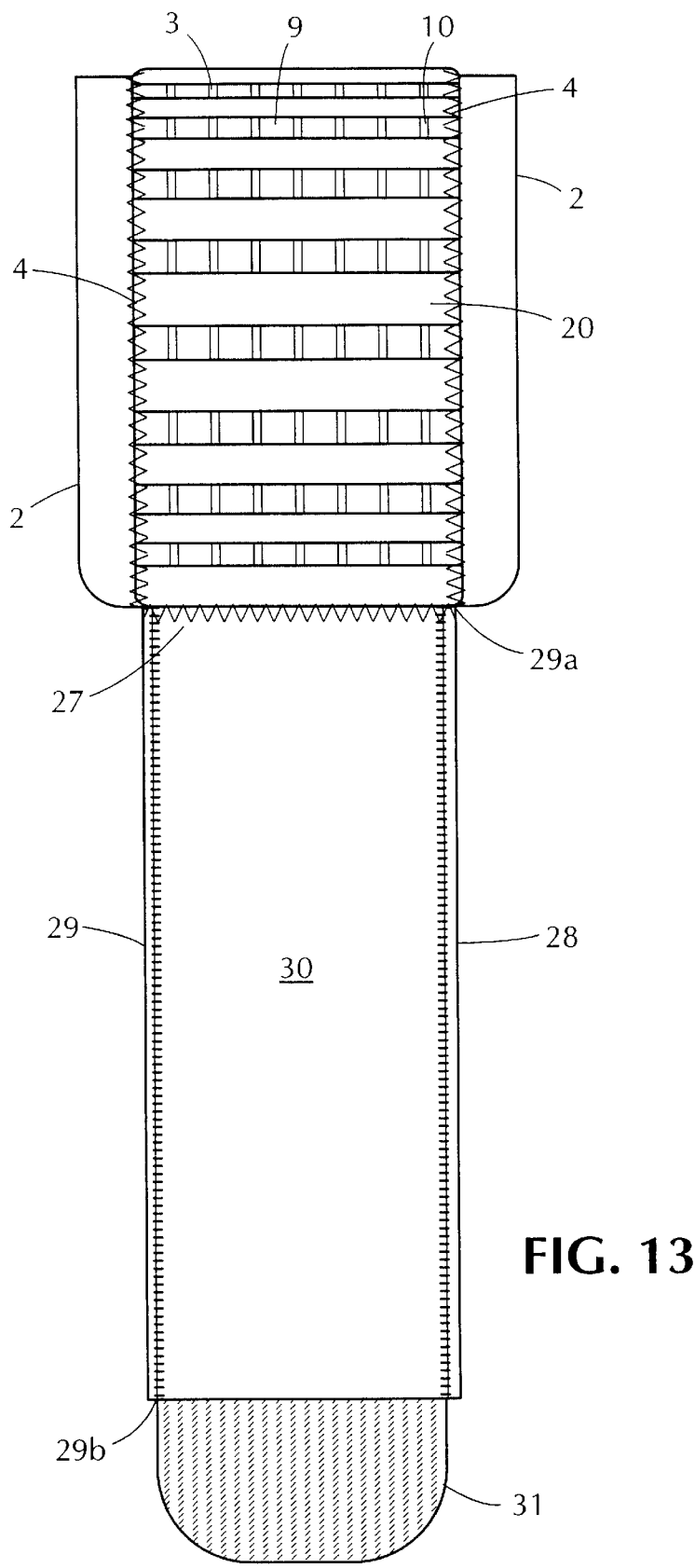
FIG. 13 is a bottom view of an example of a wrist support according to the invention with the wrist strap dis-engaged.

Referring particularly now to FIGS. 8 and 11, the exemplified wrist support defines a generally cylindrical opening 32 and is applied by slipping the hand through the generally cylindrical opening 32 so that the body 22 becomes positioned over the wrist of the user. The wrist support 21 comprises the fastening mechanism 23, comprising a stiffener (not shown), which, as depicted in FIG. 11, would be folded against a remaining portion of the body 22, and acts to keep the body 22 from moving relative to the wrist of the hand of the user while the wrist support strap 28 is being wrapped around the wrist support 21 and wrist of the user. The stiffener can be positioned along the underside of the wrist to provide support thereto. As depicted in FIG. 8, the wrist support strap 28 is then wrapped around that wrist of the user and secured upon itself by means of the fastening member 30 and securing portion 31.

FIGS. 14–22 show an embodiment of the invention where orthopedic support is configured as an ankle support 33. The ankle support 33 comprises a body 34 and at least one ankle support strap. FIGS. 14–22 show an embodiment where the ankle support comprises two ankle support straps, and lower leg strap 35 and a foot strap 36.

In the ankle support exemplified in FIGS. 14–22, the body 34 of the ankle support 33 comprises two pieces of foam material 2 and one piece of textile spacer 3. The foam material and textile spacer are the same or similar in material selection and attachment means as that described above with respect to the knee and wrist supports and otherwise having one or more protrusions 20, one or more indentations 9 and a plurality of holes 10. The foam material and textile spacer are secured together by attaching means 4, which as shown in FIGS. 14–22 may be stitching in a zig-zag type pattern.

Figure 14:
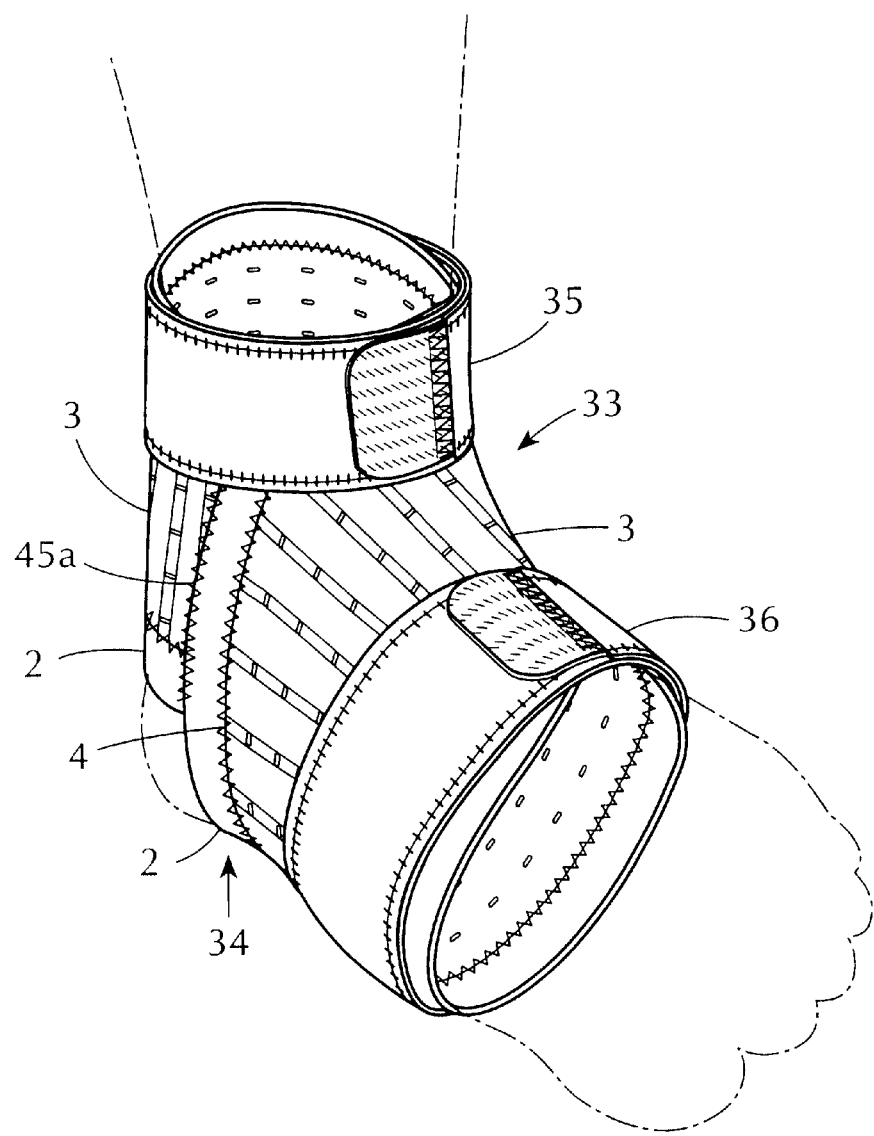
FIG. 14 is a perspective view of an example of an ankle support according to the invention depicting the foot of a user.
Figure 15:
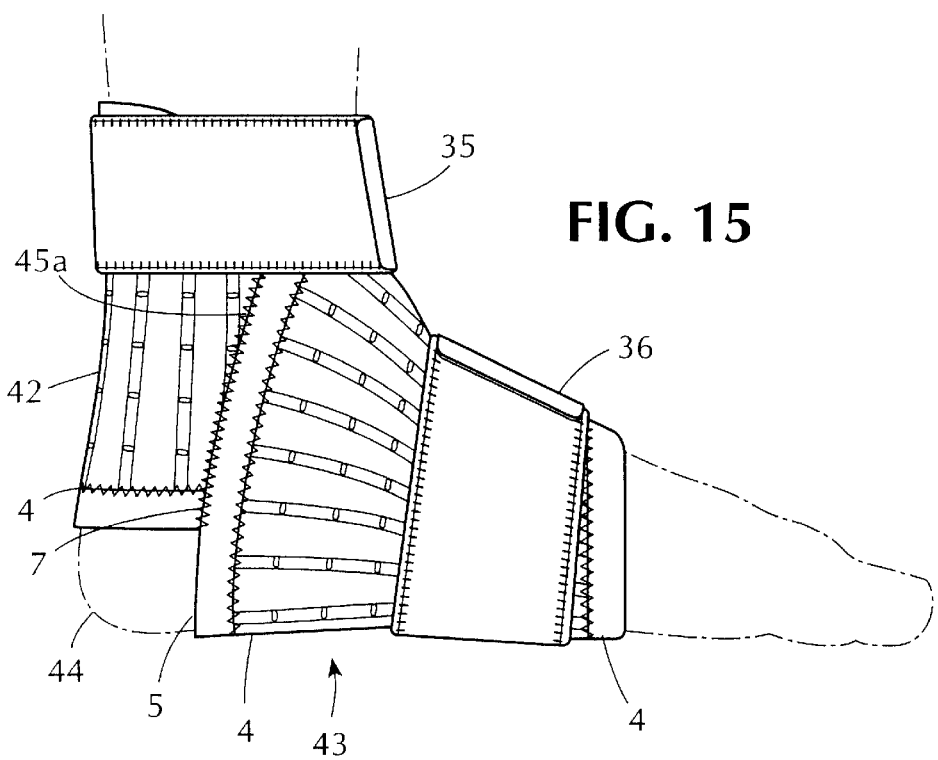
FIG. 15 is a side view of an example of an ankle support according to the invention depicting the foot of a user.
Figure 16:
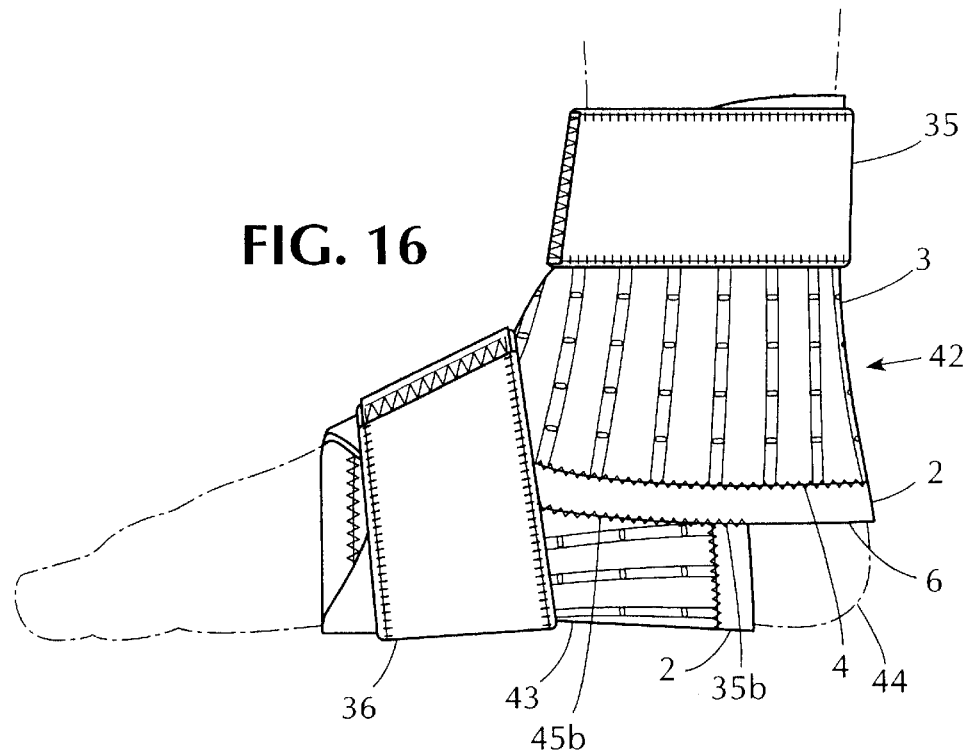
FIG. 16 is a side view of an example of an ankle support according to the invention depicting the foot of a user.
Figure 17:
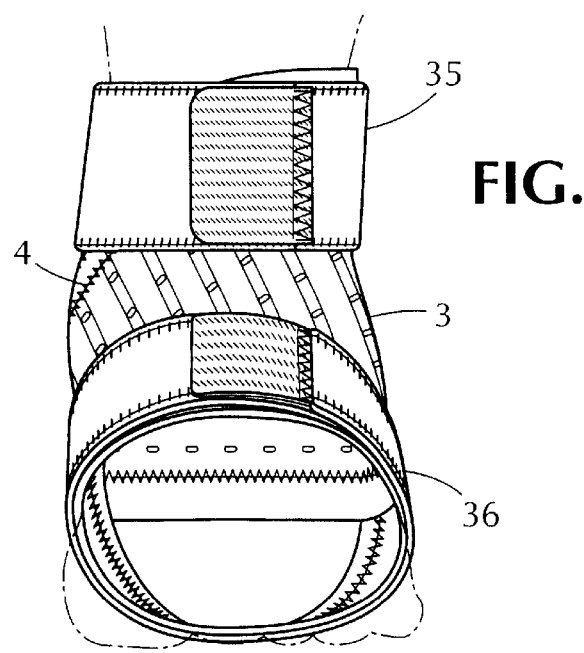
FIG. 17 is a front view of an example of an ankle support according to the invention depicting the foot of a user.
Figure 18:
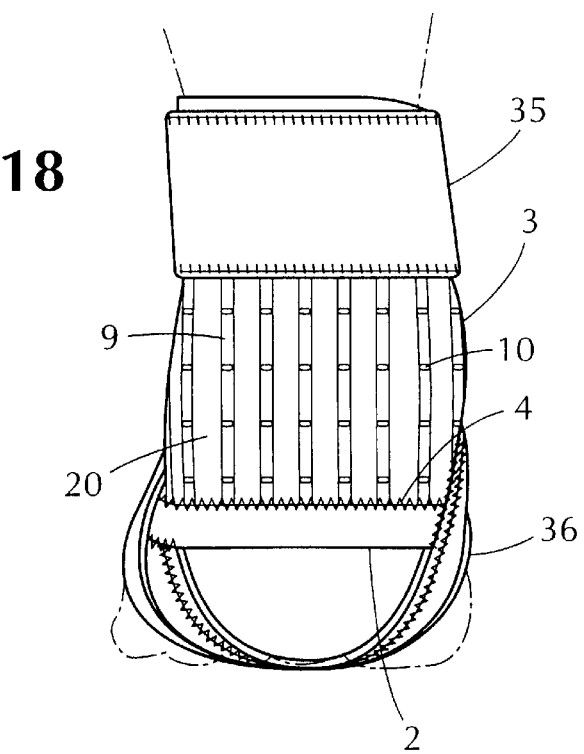
FIG. 18 is a back view of an example of an ankle support according to the invention depicting the foot of a user.
Figure 19:
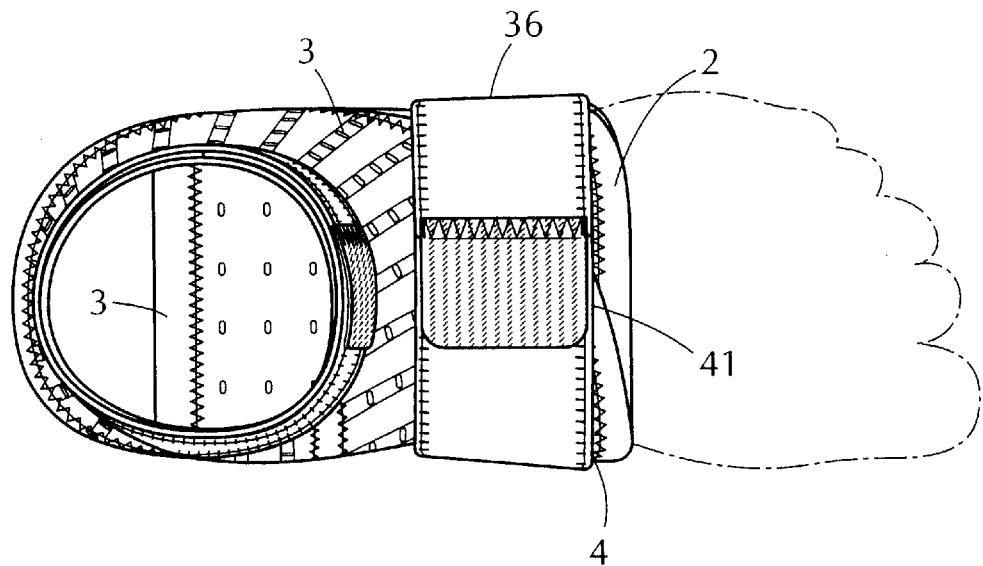
FIG. 19 is a top view of an example of an ankle support according to the invention depicting the foot of a user.
Figure 20:
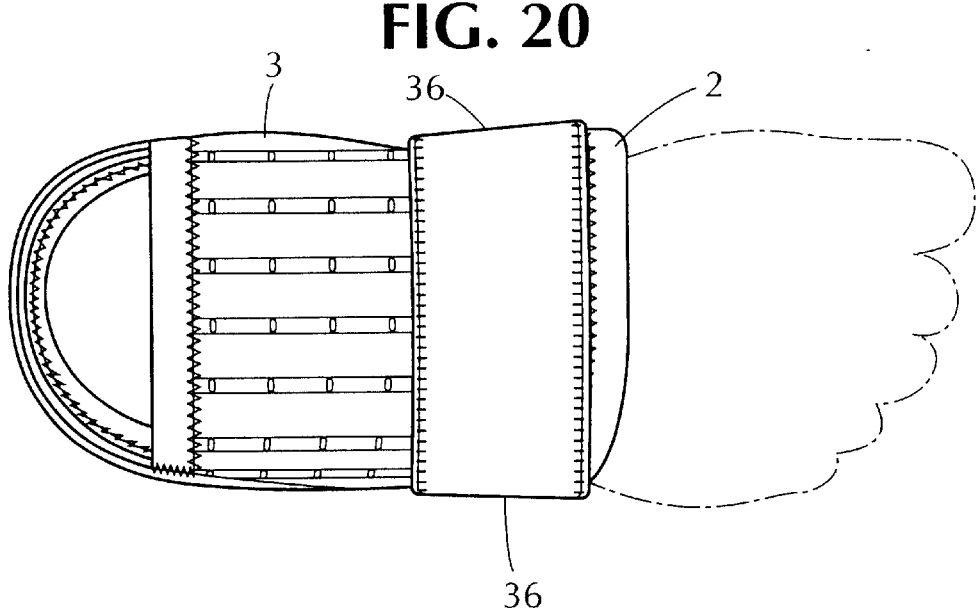
FIG. 20 is a bottom view of an example of an ankle support according to the invention depicting the foot of a user.

As shown, particularly in FIGS. 14–16, the first end 7 is secured at some point to the upper lateral side 5 and the second end 8 is secured at some point to the lower lateral side 6 both by ankle support attachment means, such as stitching, adhesive materials, binders, welding and the like which as shown in FIGS. 15 and 16 as 45a and 45b, and may be stitching in a zig-zag type pattern to form the body 34 which comprises a generally cylindrical ankle sleeve 42 having an inner surface and an outer surface and a generally cylindrical foot sleeve 43 having an inner surface and an outer surface with a heel opening 44 there between. Referring to FIGS. 14–22, the exemplified ankle support is applied by slipping the foot through the generally cylindrical ankle sleeve 42 and moving the ankle sleeve 42 to the location of the lower leg such that the heel of the user rests in approximately the heel opening 44 and the general area of the sole of the foot interfaces with the generally cylindrical foot sleeve 43. It being understood that the attachment of the first end and second end to the upper lateral side and lower lateral side are for convenience of illustration as, which should be apparent to the skilled in the art, the first end could be secured to the lower lateral side and the second end could be attached to the upper lateral side provided that the configuration forms the generally cylindrical ankle sleeve 42 and generally cylindrical foot sleeve 43 to accommodate the lower leg and foot of a user.

Figure 21:
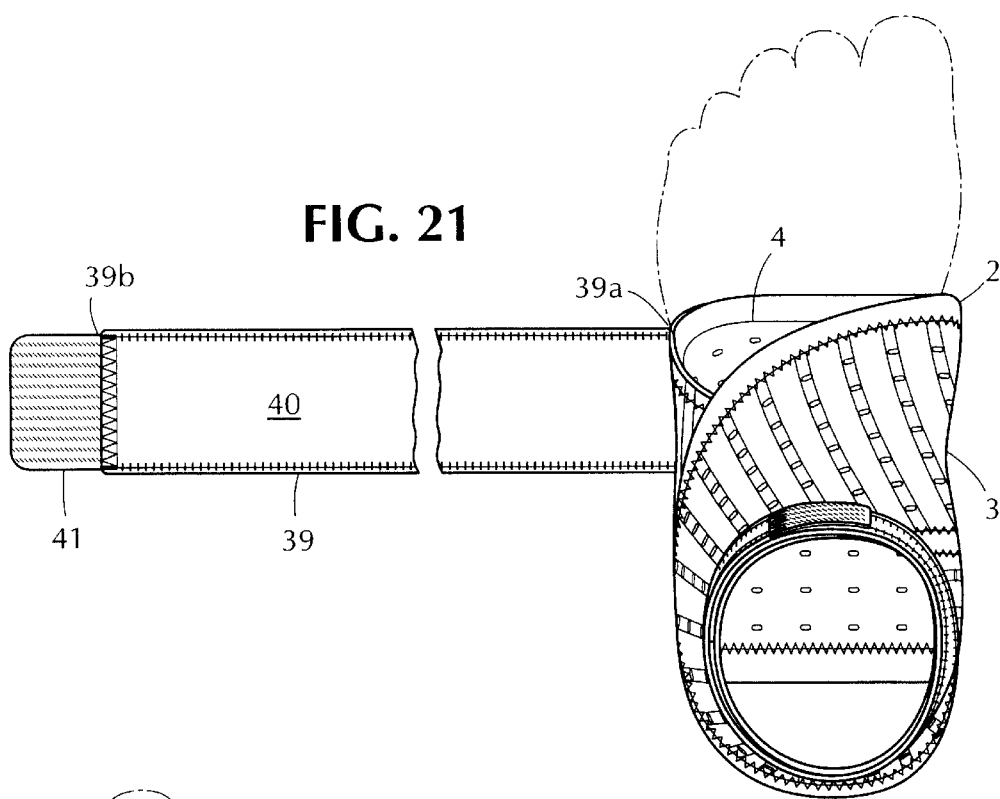
FIG. 21 is a top perspective view of an example of an ankle support according to the invention depicting the foot of a user with the foot strap dis-engaged.
Figure 22:
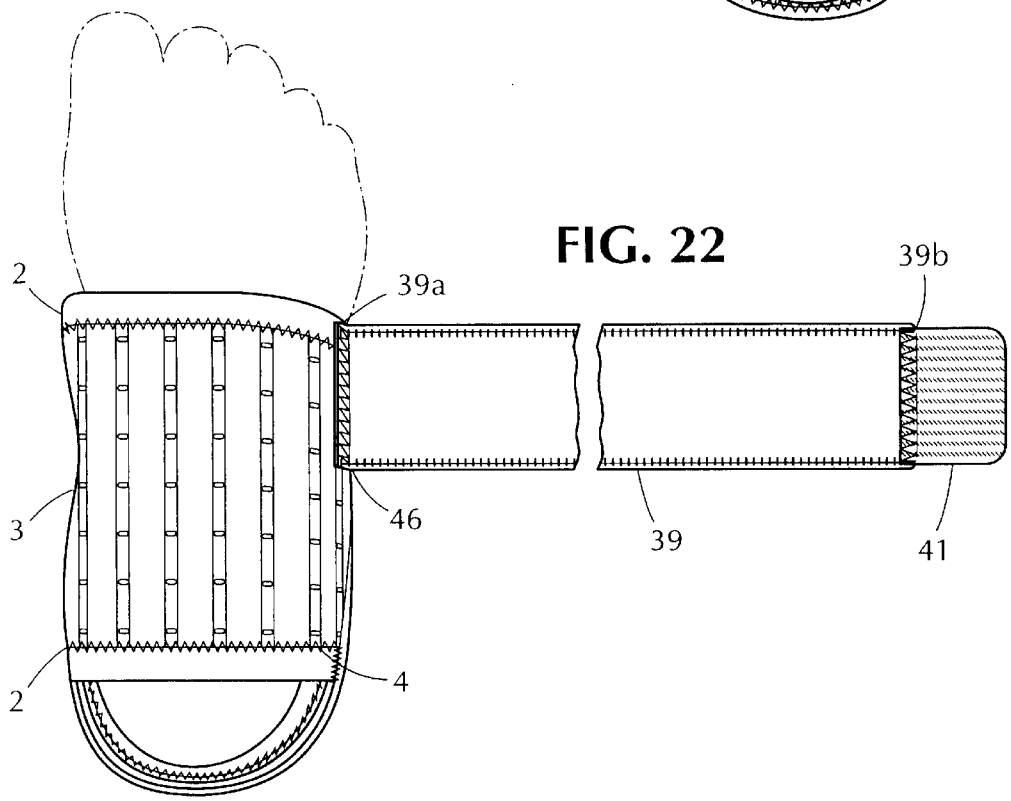
FIG. 22 is a bottom perspective view of an example of an ankle support according to the invention depicting the ankle of a user with the foot strap dis-engaged.

As shown in FIGS. 14–22, the ankle support may comprise at least one or more ankle support straps shown in FIG. 14, for example, as a lower leg strap 35 and foot strap 36, having materials and configuration the same as or similar to the wrist support strap (element 28 in FIGS. 8–13) described above. As shown in FIGS. 21 and 22 with respect to the foot strap (it being understood that the ankle support strap comprises the same features and configuration) the ankle support straps comprise a flexible portion 39 having two ends 39a and 39b, which is generally made from an elastic material having an engageable fastening member 40, such as the loop portion of a two part hook and loop type fastener which may be laminated onto one or both sides of the flexible portion 39 or may be part of one or both sides of the material of the flexible portion 39 itself. Attached to one end 39b of the flexible portion 39 is a securing portion 41 which may be part of a two part fastening system corresponding to the fastening member 40 of the flexible portion 39 the same or similar to that described with respect to the wrist support strap. For example, in the embodiment of the invention where the fastening member 40 is the loop portion of a hook and loop type fastener, the securing portion 41 will comprise the hook portion or the opposite may apply as discussed with respect to the wrist support strap. VELCRO is an example of the material suitable for the hook and loop type fastener for the ankle support straps.

The end 39a of the flexible portion of the ankle support strap opposite to that of the securing portion 41 is secured by ankle strap attachment means 46 at some point to the outer surface means of the generally cylindrical ankle sleeve 42 or generally cylindrical foot sleeve 43. In the embodiment of the invention exemplified in FIGS. 14–22, the end of lower leg strap 35 opposite to that of the securing portion 41 is secured at some point to the outer surface of the generally cylindrical ankle sleeve 42 and the end of the flexible portion of the foot strap 36 opposite to that of the securing portion 41 is secured at some point to the outer surface of the generally cylindrical foot sleeve 43, both by ankle strap attachment means 46. The ankle strap attachment means 46 may be stitching, binders, adhesives, welding and the like.

As shown in FIGS. 14–22, the lower leg strap 35 can be wrapped around the outer circumference of the generally cylindrical ankle sleeve 42 and the lower leg and the foot strap 36 can be wrapped around the outer circumference of the generally cylindrical foot sleeve 43 and the foot. In this manner the ankle support can be secured to the ankle region and therapeutic compression can be applied to the user. Exemplified in the drawings, FIGS. 14–22, the ankle support straps are engaged around the generally cylindrical ankle sleeve 42 and generally cylindrical foot sleeve 43, by disengageably fastening mechanisms such as VELCRO, however, other disengageable fastening systems may be used such as buckles, buttons and snaps.

Although the foregoing embodiments relate to knee, wrist and ankle supports, the invention includes supports for application to any joint or part of the body, for example elbow, thigh, lower leg etc. and, as with the supports described herein, all such supports comprise at least one, preferably two pieces of foam material with at least one textile spacer secured to the foam material. In all of the inventive embodiments, the sizes of the generally cylindrical portions or other body portion of the support, and the sizes, need for and number of straps are a simple matter of design choice.

It should be understood that the preceding is merely a detailed description of several embodiments of this invention and that numerous changes to the disclosed embodiments can be made in accordance with the disclosure herein without departing from the spirit and scope of the invention. Rather, the scope of the invention is to be determined by the appended claims and their equivalents.

What is claimed is:

1. An orthopedic support comprising at least two pieces of foam material and at least one air permeable textile spacer comprising one or more protrusions, one or more indentations and a plurality of holes wherein each of the at least one textile spacer is interspaced between two pieces of foam material and secured thereto by attaching means.

2. The orthopedic support of claim 1 wherein the foam material is neoprene or laminated neoprene.

3. The orthopedic support of claim 1 wherein the attaching means is selected from the group consisting of stitching, binders, welding and adhesive materials.

4. The orthopedic support of claim 1 wherein the foam material and the textile spacer have a difference in thickness of up to about 4 millimeters.

5. The orthopedic support of claim 1 further comprising at least one strap.

6. The orthopedic support of claim 5 wherein the strap comprises at least one fastener.

7. The orthopedic support of claim wherein the fastener is a hook and loop type fastener.

8. A method for supporting the joint of user comprising
a. providing an orthopedic support according to claim 5;
b. placing the orthopedic support around the joint of a user; and
c. wrapping the strap of the orthopedic support around the joint of the user.

9. The orthopedic support of claim 1 wherein the at least two pieces of foam material and at least one air permeable textile spacer secured together has an upper lateral side, lower lateral side, a first end and a second end.

10. The orthopedic support of claim 9 configured in the form of a knee support generally in the shape of a cylinder having a front, a back, a top opening and a bottom opening wherein the first end and the second end are secured by vertical attaching means.

11. The orthopedic support of claim 10 further comprising a patella opening in the front.

12. The orthopedic support of claim 10 wherein the vertical dimension of the front is larger than that of the back such that the top opening and bottom opening are angled towards each other from the front to the back.

13. The orthopedic support of claim 10 wherein the vertical attaching means is stitching, adhesive materials, welding or binders.

14. The orthopedic support of claim 9 configured in the form of a wrist support having a generally cylindrical shape comprising a fastening mechanism comprising a boxed portion having a first boxed portion end and a second boxed portion end wherein the first end is secured to the first boxed portion end and the second end is attached to the second boxed portion end, each by second attaching means.

15. The orthopedic support of claim 14 further comprising a stiffener.

16. The orthopedic support of claim 14 further comprising at least one wrist support strap having a flexible portion and a securing portion comprising an engageable fastener, the wrist support strap is secured to the wrist support at the end of the flexible portion opposite to that of the securing portion by the second attaching means.

17. The orthopedic support of claim 9 configured in the form of an ankle support wherein the first end or second end is attached at some point to the upper lateral side and the first end or second end is attached at some point to the lower lateral side to form a generally cylindrical ankle sleeve having an outer surface and a generally cylindrical foot sleeve having an outer surface with a heel opening there between.

18. The orthopedic support of claim 17 further comprising at least one ankle support strap having a flexible portion and a securing portion comprising an engageable fastener wherein the ankle support strap is secured at some point to the outer surface of the generally cylindrical ankle sleeve or generally cylindrical foot sleeve at the end of the flexible portion opposite to that of the securing portion by ankle strap attachment means.

19. The orthopedic support of claim 18 wherein the ankle support straps are a lower leg strap and a foot strap each having a flexible portion and a securing portion comprising a fastener wherein the lower leg strap is secured at some point to the outer surface of the ankle sleeve at the end of the flexible portion opposite to that of the securing portion and the foot strap is secured at some point to the outer surface of the foot sleeve at the end of the flexible portion opposite to that of the securing portion, both by ankle strap attachment means.

20. A method for supporting the joint of a user comprising providing an orthopedic support according to claim 1 and placing the orthopedic support around the joint of a user.

* * * * *

UNITED STATES PATENT AND TRADEMARK OFFICE
CERTIFICATE OF CORRECTION

PATENT NO.     : 6,582,382 B2
DATED          : June 24, 2003
INVENTOR(S)    : Domanski et al.

It is certified that error appears in the above-identified patent and that said Letters Patent is hereby corrected as shown below:

<u>Column 7,</u>
Line 48, "claim" should read -- claim 6 --.

Signed and Sealed this

Eighteenth Day of November, 2003

JAMES E. ROGAN
*Director of the United States Patent and Trademark Office*